United States Patent [19]
Griffin

[11] Patent Number: 5,702,723
[45] Date of Patent: Dec. 30, 1997

[54] MULTI-STAGE DELIVERY SYSTEM FOR INGESTIBLE MEDICATIONS OR NUTRIENTS

[76] Inventor: David Griffin, 1 Paddington Cir., Bronxville, N.Y. 10708

[21] Appl. No.: 284,815

[22] Filed: Aug. 2, 1994

[51] Int. Cl.⁶ .............................. A61K 9/22; A61K 9/28; A61K 9/52
[52] U.S. Cl. .................... 424/463; 424/457; 424/468; 424/471; 424/474
[58] Field of Search ........................ 424/465, 474, 424/463, 455, 435, 471, 457, 468

[56] References Cited

U.S. PATENT DOCUMENTS

| | | | |
|---|---|---|---|
| 2,921,001 | 1/1960 | McDermott | 424/435 |
| 3,536,074 | 10/1970 | Aufhauser | 128/222 |
| 4,271,142 | 6/1981 | Puglia et al. | 424/14 |
| 4,609,543 | 9/1986 | Morris et al. | 424/440 |
| B1 4,302,440 | 8/1986 | John et al. | 424/480 |

*Primary Examiner*—Thurman K. Page
*Assistant Examiner*—James M. Spear
*Attorney, Agent, or Firm*—Handal & Morofsky

[57] ABSTRACT

An orally ingestible multi-stage pill-like therapeutic formulation for treating a condition, said formulation having at least one internally acting ingredient providing a condition-related therapeutic effect, said internally acting ingredient being intended for dispersion in the gastro-intestinal area and a saliva-soluble material substantially coating said internally acting ingredient and comprising a second and locally acting agent providing a second condition-related therapeutic effect in the mouth, esophagus or bronchial tract. The active ingredients provide cooperative relief for one or more symptoms associated with the condition.

5 Claims, No Drawings

MULTI-STAGE DELIVERY SYSTEM FOR INGESTIBLE MEDICATIONS OR NUTRIENTS

TECHNICAL FIELD

The present invention relates to a multi-stage delivery system for ingestible medications or nutrients that could be applied to deliver beneficial or therapeutic substances, such as medications, drugs, or nutrients to the body, reducing or eliminating difficulties many people experience with the ingestion of large quantities of medication in single or multiple pill form.

BACKGROUND

The term "pill" or "pill-like" is used herein for any orally ingestible formulation in the solid state and includes tablets, capsules, caplets, lozenges and the like, as will be apparent to those skilled in the art. While such essentially solid formulations are to be distinguished from tonics, suspensions, dispersions and other essentially liquid formulations, it will be appreciated that an essentially solid pill may have a liquid or semi-solid interior.

It is of course well known that there are various coatings for medications and drugs, including, for example, U.S. Pat. No. 4,302,440 John et al, which discloses a thinly coated, easily swallowed aspirin tablet. In the case of aspirin taken for relief of headache, arthritis or other pain, or of fever or muscle soreness, clearly any delay in therapy is undesirable. John et al employs a thin coating that comprises less than 2% by weight of the aspirin tablet. As reported in column four, lines 14–19, this coating is sufficiently thin, as not to materially alter the gastric rate of disintegration as compared with an uncoated aspirin tablet. An advantage of John et al disclosure is that the coating is apparently sufficiently effective and does not have a characteristic aspirin taste or produce the esophageal discomfort of an uncoated aspirin tablet.

Typical aspirin tablets, as purchased in a drug store, have a size of 325 mg, although John et al reports in the examples column 7, line 51 a tablet weight of 405 mg. The John et al patent contains a quite extensive teaching of ingredients that can be used in a coating composition. These include the specific hydroxypropyl methylcellulose coating substance which is the subject of John et al's claims and is a film-forming agent that gives the coating its strength. In addition, plasticizers, such as glycerine propylene glycol and various other materials can be included. Optional additives which could make the tablet more palatable include flavorants, sweetening agents, and possibly deodorants, colorants and flavors. Antioxidants are mentioned even though their quantities are presumably so small so as to merely to stabilize any of the more active components of the film. The disclosure of John et al is hereby incorporated herein by reference thereto.

The John et al patent, accordingly solves a rather specific problem of getting aspirin into the stomach in a comfortable and speedy manner. John et al does nothing to overcome the more general problem addressed by the present invention, namely the problem, faced by many people, of having to take a number drugs and medications in a variety of tablets, capsules, caplets and the like, some of which may be quite large and difficult to swallow.

To try to reduce the number of individual tablets or the like that a person may have to take, other workers in the field have proposed multiple delivery systems. For example, Mehta et al U.S. Pat. No. 4,904,476 discloses a formulation which provides three distinct timed releases for systemically acting medications. The three different releases are provided by means of three different groups of spheroids which are formulated by intermixing them together in a single capsule for dispersion in the gastro-intestual system. While this teaching may be of limited value for the rather specific purpose of providing a sequence of timed releases of drugs or medications, it does not solve the general problem addressed by the present invention of reducing the number of pills or tablets by people on multiple medications.

Another conventional approach to the problem of administering multiple medications is to apply drugs or therapeutic or nutritive agents used to compound a mixture of ingredients in a single pill, capsule or tablet. Similarly, multiple doses or high-strength medications may be compounded in a single tablet. The result is a large pill, tablet or capsule, which for some people, can be extremely difficult to swallow. Colloquially, these are sometimes known as "horse pills". Many people have difficulty swallowing a single small pill size of an aspirin, yet alone huge capsules. Clearly there is a need for a simple means to alleviate the problem such people have in taking multiple pills.

SUMMARY OF THE INVENTION

The invention, as claimed, is intended to provide a remedy. It solves the problem faced by many people of having to take a number of drugs and medications in a variety of tablets, capsules and the like, some of which may be quite large and difficult to swallow. This invention solves this problem by providing an orally ingestible multi-stage pill-like therapeutic formulation for treating a condition. The said formulation has at least one internally acting ingredient, in an essentially solid medicament body, providing a condition-related therapeutic effect, with said internally acting ingredient being intended for dispersion in the gastro-intestinal area. The said formulation has a saliva-soluble material substantially coating said internally acting ingredient and comprises a second and locally acting agent providing a second condition-related therapeutic effect in the mouth, esophagus or bronchial tract. The said active ingredients provide cooperative relief for one or more symptoms associated with said condition.

Prior workers have not utilized the outer coating of a coated pill to give the patient-user an active beneficial effect and especially to provide benefits where the pill enters the body which will help a patient ingest larger quantities of medication. Prior solutions known to applicant provide passive protective, sometimes sweet-tasting coating for medications that would otherwise be unpalatable. Such coatings do not actively solve problems relating to administration of large or multiple medications.

The present invention solves these problems by utilizing an outer coating that works in conjunction with an inner layer to improve the relief obtained by the patient in a time-related manner that takes advantage of the pill's movement into the patient's body. Thus, a locally active substance, for example a local anesthetic or thick unguent coating may bring relief to a patient's throat while an inner, active ingredient works in the gastro-intestinal area or is absorbed there to act systemically. Alternatively, the outer coating may be active to ease the passage of a large pill down the esophagus by dissolving to yield a thick coating protecting the esophagus from the hard, chocking impact of the pill's profile, thus enhancing the patient or consumer's ability to ingest medication in a quantitative manner. Prior literature known to applicant does not address the quantitative aspect of the difficulties people have in ingesting medications.

DETAILED DESCRIPTION OF SOME PREFERRED EMBODIMENTS

As stated above, the composition of the invention relates to multiple therapeutic substances delivered in a single pill or other small object for oral administration. The invention provides a multi-stage delivery system in the form of a pill having an outer layer comprising an active substance or substance that will dissolve and have a beneficial effect somewhere in the mouth or upper respiratory area with the subsequent layers dissolving and the contained substances acting deeper within the body such as in the gastro-intestinal area or systemically.

To ease the administration of large pills, the outer layer or coating is relatively soft and should be rather more substantial than the coating used by John et al which has too little mass to dissolve to provide an effective lubricating coating for easy passage of large pills in the throat and esophagus. Also a thin coating may quickly expose the unpalatable aspirin interior. Instead, the inventive coating, as embodied for this aspect of the invention preferably comprises at least 5% of the mass of the pill and more preferably comprises from 10 to about 30 or 40% the mass of the pill, depending on the interior ingredients. The coating should be of a nature that dissolves rapidly and preferably has an attractive taste or flavor and includes in its composition, sweeteners or other flavorants. Materials such as hydroxypropyl methylcellulose can be used to give structural integrity to the coating and for the purposes of the present invention, the coating may be relatively highly plasticized, for example from about 30 to about 60% of a plasticizer such as those known to the art. More highly plasticized coatings can be protected from atmospheric moisture by an additional, very thin, harder coating, for example from 0.5 to 5% of the weight of the pill. Such an additional coating is preferably quick-dissolving and the pill may be accompanied by instructions to retain it in the mouth long enough to dissolve the hard outermost coating and expose the plasticized layer.

While a principle merit of the invention as described above resides in its application to rather larger pills some advantage can also be obtained by using a relatively soft unguent coating on somewhat smaller pills. Many people have great difficulty in swallowing any size pill and the inventive lubricitive coating can help such people swallow pills of any size.

Although helpful with small pills, such as a typical aspirin tablet of 325 or 405 mg, it is envisioned that this aspect of the invention is primarily applicable to the larger pills of at least 500 mg in size and more commonly in the range from 600 mg to about one gram. While the invention is clearly of great advantage with pills of any such large size that are capable of being swallowed, it believed that this limit is probably around two grams.

If desired, the soft outer coating can also provide a vehicle for a locally absorbed medication while the interior, which can be a relatively hard, unpalatable or friable active substance which is nevertheless suitable for gastric disintegration and absorption, can contain a second medication or therapeutic or nutritive agent, the two medications cooperating to provide therapy for a common condition. In addition to facilitating the ingestion of large doses, this invention solves a problem faced by many people in ingesting multiple doses of multiple medications or therapeutic nutritional supplements by formulating these materials in a new and useful manner. To this end, the invention provides a multi-stage delivery system for medications or therapeutic or nutritive agents which comprises an internal gastrically or systemically acting ingredient coated with a substantial coating containing or constituting a saliva or mucous fluid-soluble material which is formulated with a second active agent which acts locally in the mouth.

This novel system can provide a number of advantages in treatment of many maladies. A primary advantage is the ability to absorb many separately acting active ingredients in a single pill in a manner which can be controlled in time and space, or point of action in the body. Interesting benefits, can be obtained, such as an amplification or deamplification of an interaction between the active ingredients, if such an interaction is desired or is to be avoided. The time and space absorption can be controlled by providing one or more inert layers in between the active ingredients. The thickness and composition of such an inert layer and either the rate of dissipation of the layer or the rate of diffusion of therapeutic agents through the material or both can determine the timing of the release of active ingredients. Some examples of such a material for the layer could be hydroxypropyl methylcellulose or other modified EVAC celluloses, (ethyl vinyl acetate copolymer) or other suitable materials known to those skilled in the art for providing coating layers on medications.

One example of a two-stage delivery system according to this embodiment of the invention is a cold capsule including a pain reliever or antipyretic in an external unguent coating such, for example acetaminophen in a modified cellulose coating sweetened to be tolerable to the palate, and an antihistamine for example diphenhydramine hydrochloride, which is a particularly bitter substance can be delivered in the second stage interior of the inventive capsule for gastric absorption. The pain reliever acts locally to treat any painful throat conditions accompanying the cold, and to provide a route of rapid absorption, while the antihistamine relieves congestion systemically.

Another two-stage coated capsule may have a treatment for a sore throat in an outer coating and a pain reliever or antihistamine or some such combination of traditional cold ingredients in a second-stage interior of the capsule.

Another useful embodiment is a two-stage coated capsule or tablet having an outer coating comprising an antacid such as calcium carbonate, magnesium hydroxide or potassium nitrate and an inner layer comprising a suitable antibiotic for example amoxicillin. Such a novel capsule provides an advantageous treatment for a mild stomach infection, addressing both the short term problem of an upset stomach and systemically treating the infection causing the symptoms. The time and space absorption of the two active ingredients could be controlled by a median inert layer to avoid any unwanted chemical interactions between the active ingredients. Such antacid coating can be applied to any chemically and physiologically compatible medication. The value of such a two-stage antacid coated medicament is not limited to people suffering from stomach infections. Many people have sensitive stomachs and can suffer heartburn or simlar discomforts that are relierable by buffering when the stomach is disturbed by the arrival of one or more rather large or unpleasant capsules or tablets. Such acid-related discomforts can be relieved by the two stage-stage buffer-coated medications according to this embodiment of the invention which provide a soothing effect upon impact with the stomach, quelling any disturbances, enabling an inner layer drug or medicament to be absorbed in comfort.

An alternative coating for a large capsule, according to the invention, in addition to an unguent-producing layer, could contain a small amount of local anesthetic for example benzocaine to permit relatively large or difficult pills to be swallowed by people with throat disorders, such as a simple sore throat, after effects of surgery or throat or esophagus disorders that render the passage to the stomach particularly sensitive to the passing of any form of capsule.

A treatment for chronic halitosis, or temporary halitosis after surgery, could be a pill with an outer layer comprising a mouth deodorizer and a breath freshener such as chlorophyll to alleviate the odor, optionally with flavorants or colorants or both, and an inner layer comprising a suitable antibiotic such as a broad-spectrum tetracycline to attack the bacteria in the gastro-intestinal system causing the bad breath. This system would address both the immediate problem of bad breath symptoms and provide long-range therapy for the underlying condition.

For a person suffering the common condition of lactose intolerance, getting an adequate amount of calcium-bearing dairy products can be difficult since ingestion of lactose causes gas, bloating, and stomach irritation. Calcium deficiencies attributable to a lack of dairy products in one's diet may cause dental problems such as cavities and gingivitis. Twin-pronged therapy for these problems may be found in the form of a capsule which contains fluoride in a substantial outer coating to dissolve in the mouth and providing a localized fluoride treatment to strengthen and possibly repair the teeth. An inner layer could contain a calcium supplement for systemic absorption from the stomach to strengthen the teeth as well as bones. A further, optional innermost layer can contain a time-release formulation of lactase enzymes for continuous release throughout the day to break down ingested lactose. After ingestion of this capsule, a patient can consume modest amounts of dairy foods throughout the day thereby to increase their intake of calcium while simultaneously receiving therapy for the dental consequences of the past deficiencies. Compound formulation of multiple agents into a single dose is of special value for children who can be expected to have difficulty managing multiple pills.

In another embodiment of the invention a multi-stage influenza treatment pill has an outside coating or layer including a pain reliever such as acetaminophen and a small amount of a local anesthetic such as benzocaine to relieve initial throat pain along with flavorants to make it tolerable to the palate. An optional inner layer contains a volatile agent such as menthol to work directly in the bronchial tube area and soothe or relieve any bronchial congestion purposes. Another optional interior layer could contain a decongestant such as phenylaprine hydrochloride and an antihistamine such as hydroxyzine hydrochloride with antinausea properties to alleviate some of the nausea experienced by influenza suffers. A further, or alternative inner layer would contain an antibiotic such as amoxicillin along with stomach buffers for gastric dispersion to treat gastric symptoms and soothe the stomach. To combat the debilitating effects of a virus, a vitamin supplement can be added to the pill to boost the patient's strength and disease resistance. Such a four-stage capsule addresses the treatment of multiple symptoms associated with certain influenza infections providing control over the timing and the distribution of medicaments in the body while reducing the number of individual pills that the patient has to ingest.

Other such combinations of ingredients will be apparent to those skilled in the art. Such modifications are within the spirit and scope of the invention, which is limited and defined only by the appended claims.

While some illustrative embodiments of the invention has been described above, it is, of course, understood that various modifications as to the nature and proportions of ingredients, taking into account any interactions between active ingredients will be apparent to those of ordinary skill in the art.

I claim:

1. An orally ingestible multi-stage pill or capsule to treat a condition, said pill or capsule having multiple active ingredients and comprising:

a) an internal layer comprising an essentially solid first active ingredient, being an internally or systemically active ingredient intended for absorption gastro-intestinally;

b) an antacid coating said first active ingredient to relieve discomfort caused by the ingestion of said multi-stage pill or capsule; and c) an external layer comprising a second active ingredient being a solid or semi-solid saliva-soluble material, said second active ingredient being substantially formed around the antacid coating and being a second and locally acting agent providing a condition-related therapeutic effect in the mouth, esophagus or bronchial tract;

said first and second active ingredients providing cooperative relief for one or more symptoms associated with said condition.

2. A pill or capsule according to claim 1 wherein said external layer comprises about 20 percent to 70 percent of the mass of said pill or capsule and is sufficiently thick to prevent said internal layer from being exposed in the mouth when swallowed.

3. A pill or capsule according to claim 1 wherein said external layer is soluble in saliva and of sufficient mass to provide effective lubrication in the throat.

4. A pill or capsule according to claim 1 wherein the external layer further comprises a hydrophilic gel to dissolve in the mouth to provide an unguent layer.

5. A pill or capsule according to claim 1 wherein said internal layer comprises sustained release medication or therapeutic substances.

* * * * *